United States Patent [19]
Kuusi

[11] Patent Number: 4,696,023
[45] Date of Patent: Sep. 22, 1987

[54] PROCEDURE AND MEANS FOR MEASURING WITH AID OF AN X-RAY TUBE THE DISTRIBUTION OF FILLERS OR EQUIVALENT IN A WEB

[75] Inventor: Juhani Kuusi, Helsinki, Finland

[73] Assignee: Robotest Oy, Finland

[21] Appl. No.: 638,472

[22] PCT Filed: Nov. 30, 1983

[86] PCT No.: PCT/FI83/00076

§ 371 Date: Jul. 30, 1984

§ 102(e) Date: Jul. 30, 1984

[87] PCT Pub. No.: WO84/02191

PCT Pub. Date: Jun. 7, 1984

[30] Foreign Application Priority Data

Dec. 1, 1982 [FI] Finland .................................. 824142

[51] Int. Cl.⁴ .................... G01N 22/223; G01N 33/34
[52] U.S. Cl. ........................................ 378/46; 378/45; 378/53; 378/90
[58] Field of Search .................. 378/45, 46, 48, 50, 378/90

[56] References Cited

U.S. PATENT DOCUMENTS

| | | | |
|---|---|---|---|
| 3,102,952 | 9/1963 | Hendee et al. | 378/45 |
| 3,530,296 | 9/1970 | Lehtinin et al. | 378/45 |
| 3,914,607 | 10/1975 | Cho et al. | 250/385 |
| 4,081,676 | 3/1978 | Buchnea | 378/46 |
| 4,147,931 | 4/1979 | Puumalainen | 378/50 |

FOREIGN PATENT DOCUMENTS

| | | | |
|---|---|---|---|
| 1773085 | 3/1972 | Fed. Rep. of Germany . | |
| 2727505 | 1/1979 | Fed. Rep. of Germany | 378/45 |
| 2946567 | 6/1980 | Fed. Rep. of Germany . | |
| 3219962 | 12/1982 | Fed. Rep. of Germany . | |

OTHER PUBLICATIONS

"Determination of Content and Distribution of Filler . . . ", J. Kuusi, Paperi Puu 52, No. 4a, pp. 145-151, 154-158 (Apr. 1970).
English Abstract from Paperchem, access No. 50-06512, Karton No. 3, 8(1979) "Monitoring Apparatus for Determining . . . ".
English Abstract from Paperchem, access No. 46-03646, Prom No. 17: 1974 pp. 123-126, "Use of X-Rays for Determining . . . ".

Primary Examiner—Carolyn E. Fields
Attorney, Agent, or Firm—Steinberg & Raskin

[57] ABSTRACT

A procedure and means for non-destructive measuring of the distribution in the thickness direction of the filler and/or coating materials in paper or cardboard. Radiation emitted by an x-ray tube is used to excite in the material component to be examined, its characteristic x-ray radiation, the intensity of this radiation being observed. Measurements are made on both sides of the specimen. The contents of other filler components are also determined by x-ray absorption measurements, and the base weight of the paper, e.g. by beta radiation absorption. Measurements of the characteristic radiation, elicited with constant energy x-ray radiation as well as absorption measurements of radiation obtained directly from the x-ray tube and of radiation produced in transformation targets are made in order to eliminate by calculation the disturbing interaction of the filler components. Alternatively, distribution measurements are made with the aid of characteristic radiation elicited with radiation from the x-ray tube varying in a known manner during the measuring cycle and by measuring its absorption followed by equivalent calculations.

29 Claims, 15 Drawing Figures

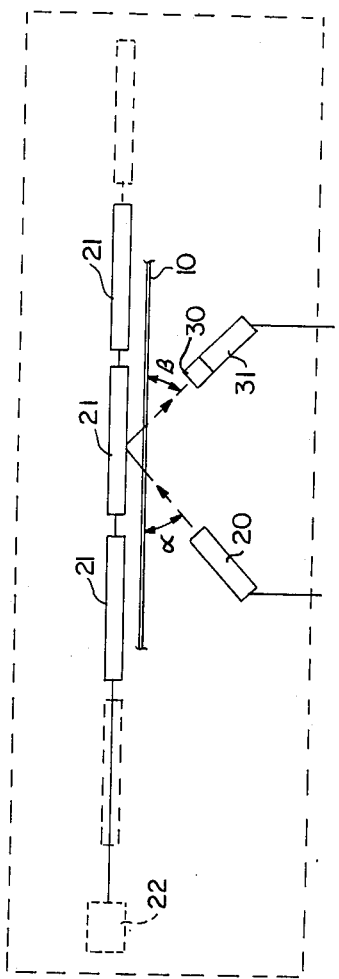

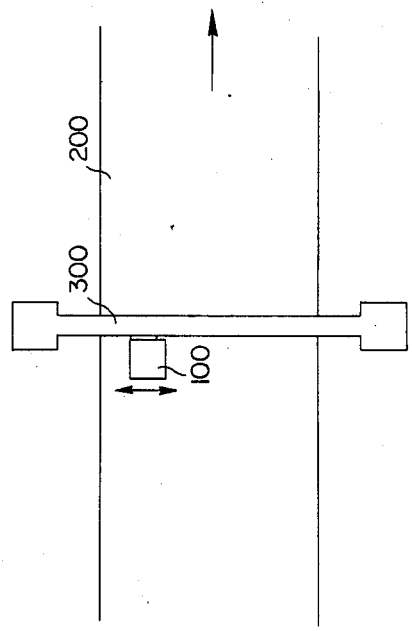

PROCEDURE AND MEANS FOR MEASURING WITH AID OF AN X-RAY TUBE THE DISTRIBUTION OF FILLERS OR EQUIVALENT IN A WEB

BACKGROUND OF THE INVENTION

The present invention concerns a method for measuring the distribution in the thickness direction of filler and/or coating materials of paper, cardboard, or the equivalent, and the contents of said materials without destroying the sample. In the method or procedure of the invention the radiation emitted by an x-ray tube is used to excite in the material component under examination of the object under measurement its characteristic x-ray radiation and the intensity of this radiation is observed. In this procedure, measurements are carried out on both sides of the specimen under examination. In addition, the contents of other filler components are determined by x-ray radiation absorption measurements, in order to eliminate the effects of such components interfering with the distribution measurement, and the base weight of the paper is determined by beta radiation absorption measurement, or by another equivalent procedure.

Furthermore, the present invention concerns apparatus applying the method and novel uses of the procedure and the apparatus.

When paper and paper machines are discussed in the following, reference is generally made both to paper and cardboard, and respectively both to paper and cardboard machines.

Fillers, which as a rule are mineral substances, are incorporated in the paper primarily for their effect of improving the printing technological properties. Fillers are most commonly used for printing papers. The filler addition improves the opacity, lightness, printer's ink absorption and surface smoothness of the paper. The fillers influence-in a particularly advantageous manner the quality of paper to be glazed.

It is known in the art to add filler material in two ways, either by mass filling or by coating. In the mass filling method or procedure, the filler material is added in the form of suspension to the pulp sludge before the arrival of the sludge on the paper machine, whereby the filler material is admixed with the entire fiber material in the finished paper. In the coating procedure, a suitable glue substance is admixed with the filler material in the aqueous phase, such as starch or casein, whereafter the surface of the paper is brushed with this mixture in a continuous process.

The filler materials in paper tend to be non-uniformly distributed in the thickness direction of the paper, causing one-sidedness of the paper. The one-sidedness of paper manufactured on Fourdrinier machines is due to the fact that the fillers are washed out together with the water that is drained, from the lower part of the pulp web into the drainage water, whereby they become enriched in the upper part of the web. As is known in the art, efforts have been made to reduce the problems of one-sidedness, not only by additives improving the retention, but also by gentle dewatering at the initial draining phase, which requires a longer dewatering time and therefore implies lengthening the wire section or reducing the speed of the paper machine.

In machines with a planar wire, the difficulties with the fines and filler distribution manifest themselves when papers for offset printing are manufactured. A high filler and fines content on the top surface of the paper caused dusting, which is a serious detriment in the offset process. In contrast, papers manufactured on a twin wire machine are considered well appropriate for offset printing. This is due to the symmetrical shape of the fines distribution and to equal leaching of both surfaces of the web due to two-sided dewatering. It is in fact generally held that due to move uniform fines distribution, the printing by offset on paper manufactured on a twin wire machine is more successful than that on paper manufactured on a Fourdrinier machine. Offset printability has indeed increased in significance because offset printing is increasingly replacing the letterpress printing procedure.

On the other hand, the filler content of the surfaces of the paper web cannot always be brought to desired level with a twin wire former. Even when planar wires are used, only the top side of the web (the side facing away from the wire) is satisfactory as to its filler content. The low filler content of the web surfaces is particularly problematic in so-called SC gravure papers. Attempts may be made to increase the filler content of the paper surfaces by increasing the filler content of the pulp in the headbox, but even with this expedient, a satisfactory condition is not achieved, because of the aformentioned poor retention characteristic of the filler and of its enriching in the inner parts of the paper. In addition, when the filler content in the headbox has to be increased, the consistency in the headbox is likely to become excessive so that it impairs the formation of the paper.

Modern high-speed printing presses impose particularly high requirements on the printing paper. These requirements are based on trouble-free operation of fast printing presses and on the appearance of the printing. The imprint is considerably influenced by the symmetry between the sides of the paper and the quality of the surfaces of the paper, which is naturally also influenced by the distribution of the fillers. Heretofore, no methods or procedures and apparatus have been in use with which the filler distribution could have been measured even on line either on the paper machine, on the printing press or on the paper coating means.

It is known in the art, as described in Finnish Pat. No. 40587, inventors Juhani Kuusi and Antti Lehtinen and applicant Valmet Oy, to excite the characteristic x-ray radiation of the filler material by radiations, such as alpha, beta, gamma or x-ray radiation, penetrating to various depths in the paper, and in this way to gain information on the vertical distribution of the filler. The procedure has been described in greater detail in a paper by J.Ized "Determination of Content and Distribution of Filler and Coating Materials in Paper Using Radioisotope X-Ray Spectrometry," Paper and Timber No. 4A, 1970. As was observed in the paper, variations in relation to each other of the filler contents cause certain effects of which the quantitative elimination by the procedures described in the paper is impossible. This has impeded the introduction to practice of such procedures.

The state of art regarding filler measurements is illustrated in general by a publication of April, 1982 by Buchnes A., McNeiles L. A. and Hewitt J. S., entitled "The Application of X-Ray Absorption and Fluorescene Analysis to the Measurement of Paper Additives," Int. J. Appl. Radiat. Isot. Vol. 33, pp. 285 to 292 (1982), where a fluorescene and absorption technique is used for determining the total contents of different fillers, based on the assumption that the fillers are uniformly distributed in the thickness direction of the paper. In practice, this is hardly ever the case. It is thus understood that there are no endeavours whatsoever made in this publication to determine the important thickness-direction distribution, nor has it even been taken into account as a potential source of error in determination of the total filler content. It should be noted, however, that in the instances described in the paper, the influence of the source of error is minimal.

Procedures capable of determining the filler distribution and the total filler content directly in the paper machine are not in use at all.

SUMMARY OF THE INVENTION

The principal object of the invention is to provide a new method or procedure and apparatus suited, in addition to laboratory measurements, for the measurement of filler distribution, which method and apparatus make possible the control and adjustment of the manufacturing process in a paper machine on the basis of filler distribution measurements.

An object of the invention is to provide a method and apparatus for determining the thickness-direction filler distribution in the paper and the total filler contents either in the laboratory or directly in a paper machine, on line.

Another object of the invention is to provide a procedure and apparatus for determining the thickness-direction filler distribution in the paper and the total filler contents when the contents of different filler components, such as, for example, $CaCO_3$, $TiO_2$, kaolin, talc or equivalent, are variable.

Still another object of the invention is to provide an opportunity not only for immediate product quality control directly in the machine, on line, but also an entirely new possibility of controlling the paper manufacturing process, the significance of which is emphasized when efforts are made to manufacture printing paper meeting over greater quality requirements at lowest material costs. Yet another object of the invention is to measure and control the distribution, which provides an opportunity to develop the paper machine construction and the total control systems of paper machines.

Another object of the invention is to provide a method which is suitable for quality control of the paper fed into fast modern printing presses, and possibly for the control and/or adjustment of the operation of the printing presses.

To achieve the aims presented in the foregoing and those which will hereinafter become apparent, in a first embodiment of the method of the invention, the distributions or fillers and equivalent are determined by combined processing of the two following sets of measurements.

1. Absorption meansurements for determining the contents of different filler components with radiation obtained directly from the source or produced with its aid in appropriate transformation targets; as many measurements as there are filler components to be considered separate ones.

2. Measurements of the characteristic radiation of the material components excited in the paper by different sources of radiation.

In a second embodiment of the method of the invention, the distribution measurements of fillers and equivalent are performed with the aid of measurements of the characteristic radiation of the material components excited in the specimen by radiation obtained from an x-ray tube and varying in a known manner during the measuring cycle, and with the aid of absorption measurement of the same radiation, such absorption measurement being for use in elimination by calculation of the disturbing effect of the variations of the filler components' contents in relation to each other.

A first embodiment of the apparatus of the invention in turn mainly comprises a measuring head having an x-ray tube emitting constant energy radiation and a transfer mechanism therefor, and radiation transformation plates and transfer mechanisms therefor, and radiation detectors and pre-amplifiers. The measuring head is connected to a measuring device having power sources, an amplifier and a counter, processor and display unit.

A second embodiment of the apparatus of the invention comprises a measuring head with an x-ray tube emitting radiation varying in energy during the measuring cycle in a known manner, and radiation detectors and pre-amplifiers. The measuring head is connected to a measuring apparatus comprising power sources, amplifiers and a multi-channel counter, processor and display unit using a time axis.

The method or procedure and apparatus hereinbefore described are used, as taught by the invention, for example, in a paper machine, in on-line measurement for measuring the filler distribution in the thickness direction and the total filler content of paper. In addition, the obtained measurement results may be used as feedback signals in the control system of the paper machine, in the control of the filler distribution, and/or of the total filler content of various filler materials. An advantageous application of the invention is in measurement, and possibly in the control, of the coating material content and/or coating material distribution in paper or cardboard that is either being coated in an on-line process or has been tested in a separate coating apparatus, in particular of its one-sidedness. of the paper being fed into a printing press and/or governing, and possibly controlling, the operation of the printing press.

As has in part become apparent from the foregoing, the inventive idea is that the intensity of the characteristic x-ray radiation of the filler component excited with different radiation sources, and possibly with different angles of incidence of the exciting radiation, is measured on both sides of the paper. This intensity provides information about the shape of the distribution. In addition, in this x-ray fluorescence measurement it is possible to determine the intensity of the exciting radiation scattered back from the paper and which correlates, for example, with the base weight of the paper. This would serve as an auxiliary quantity in the processing of results. What is significant from the point of view practical applications is that the contents of various filler components are measured by x-ray absorption measurements. These measurements make use of the primary radiation, possibly varying as to its energy with reference to time during the measuring cycle, emitted by an x-ray tube and radiation with desired absorption properties which has been derived therefrom, or from an x-ray tube placed on the other side of the paper, with the aid of appropriate transformation targets. The auxiliary quantity is the absorption measurement signal of beta radiation used as routine in measurements on paper for determinations of base weight in $g/m^2$ (fibers plus filler). Based on the results of the absorption measurements, it is possible by calculation to eliminate the effects of the variation of the different filler components' contents on the fluorescence measurements, and in this manner to determine the filler distribution and the contents of different filler components.

In the laboratory, the invention affords an opportunity for a rapid quality control of the paper, and thereby for the control of the manufacturing parameters with a given lead time. Particularly the filler distribution close to the surface layers of the paper has considerable significance concerning the printability of the paper. Furthermore, a distribution of proper shape provides an opportunity to use filler in abundance, thereby lowering the total material costs. The procedures or methods presently used in laboratories, such as dividing the paper into different layers by a tearing tape, incineration of layers and ash determination, are slower by one order of magnitude and more inaccurate than the method of the invention.

BRIEF DESCRIPTION OF THE DRAWINGS

For a fuller understanding of the invention, reference is had to the following description, taken in connection with the accompanying drawings, in which:

In FIG. 5C, the solid line graph represents the result of measurement obtained from the top side of the paper shown in FIG. 1, and the interrupted line graph represents the corresponding result of mesurement obtained on the wire side;

FIG. 8 is a schematic diagram of a measuring head disposed on a transverse measuring beam for reciprocating movement over the paper web.

DESCRIPTION OF PREFERRED EMBODIMENTS

Figure 1:
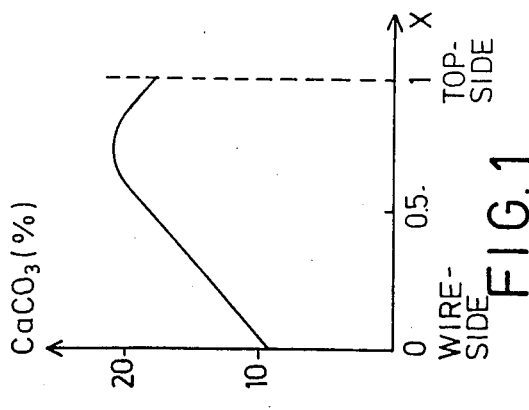
FIG. 1 is a graphical presentation of a typical filler distribution in paper manufactured on a Fourdrinier machine.

A typical filler distribution of paper in its thickness direction x is shown in FIG. 1. The filler is least in quantity on the wire side. In this instance, the maximum is reached slightly above the center point of the paper, marked 0.5 on the horizontal axis. The filler content decreases towards the top surface ($x=1$).

The attenuation or extinction of x-ray, gamma and beta radiation in matter can generally be expressed by the exponential formula:

$$I = I_o e^{\mu m},$$

where I (l/s) is the intensity of the radiation that has gone through a mass course m (g/cm$^2$), $I_o$ (l/s) is the original intensity of the radiation and $\mu$ (cm$^2$/g) is the absorption coefficient representing the extinction or attenuation capacity of the material.

Figure 2:
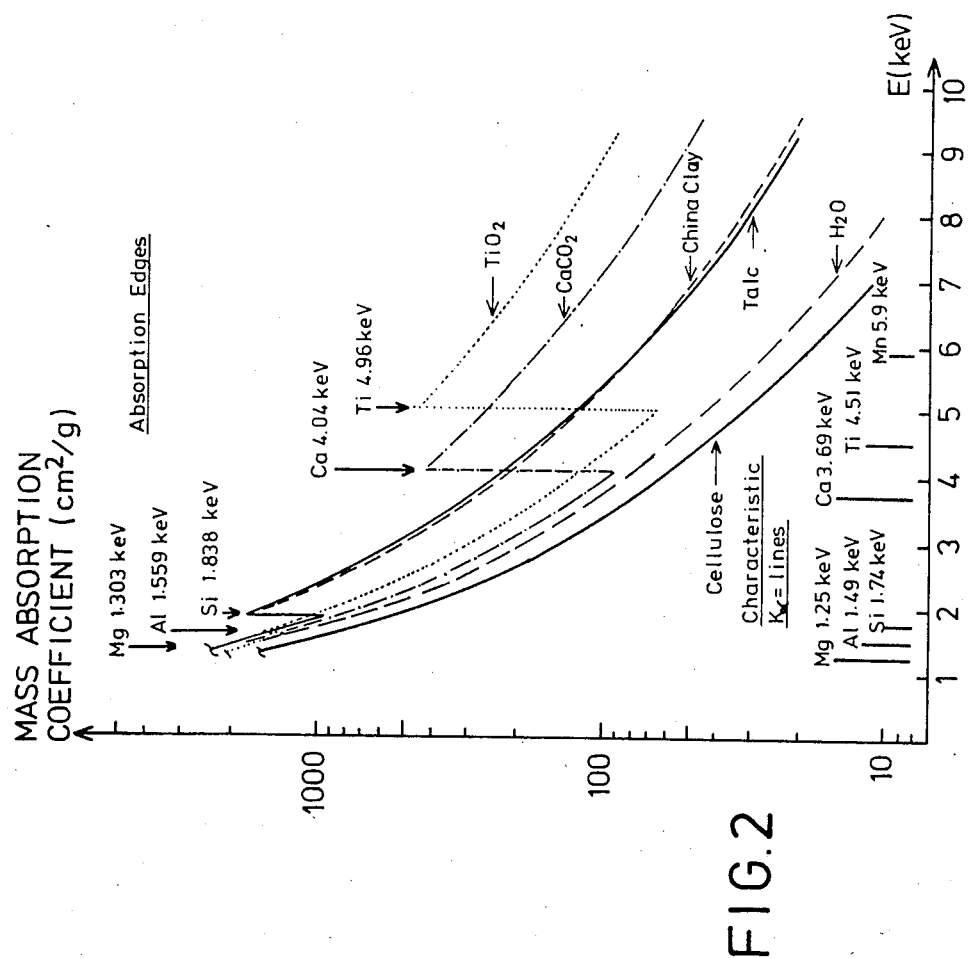
FIG. 2 is a graphical presentation of mass absorption coefficients of some mineral filler and coating materials of paper, of water and of cellulose for low energy x-ray radiation.

The absorption coefficients for low energy (1 to 10 keV) x-ray and gamma radiation of materials which are important in view of filler measurements are set forth in FIG. 2, plotted over energy. Both are the same type of electromagnetic radiation. In FIG. 2 the abscissa represents the energy (in keV) and the ordinate represents the absorption coefficient $\mu$ (in cm$^2$/g). With the exception of a few discontinuous irregularities, the absorption coefficient, and therefore also the attenuation in the material, decreases with decreasing energy. However, some of the discontinuous jumps seen in the curves of FIG. 2 are of central importance in the embodiments of the invention. If the graph of the absorption coefficient of calcium carbonate ($CaCO_3$) is scrutinized, we find that it descends smoothly throughout the range from 1 to 4 keV, until, at 4.04 keV energy, its value discontinuously increases to be tenfold and thereafter once more decreases smoothly with increasing energy of the radiation. The physical cause underlying this jump is that: in the range under consideration, x-ray and gamma radiation are attenuated in the material in the manner that the energy of the radiation quanta transfers totally to electrons in the atoms. Such electrons, by virtue of the energy imparted to them, are flung out from the atom, leaving behind a vacancy in the electron shroud. The energy of the x-ray or gamma quantum has to be higher than the binding energy holding the respective electron to its atom. When the energy of the radiation is lower than the 4.04 keV corresponding to the jump in the graph for $CaCO_3$, the radiation is not able to detach the electrons of its inner shell (the K shell), which are the electrons most strongly bound to the atom, from the calcium atom. When the energy of the incident radiation surpasses this limit, its quanta can become absorbed in the substance by detaching electrons from the inner shell, and this exactly gives rise to the discontinuous increment of the absorption coefficient. The higher the atomic number of a substance, in practice, usually the heavier it is, the higher is the energy at which is found this K absorption limit, that is, the absorption limit corresponding to the K shell.

Thus, it is shown in FIG. 2 that the K absorption limit, due to titanium, of titanium dioxide ($TiO_2$) is located at an energy of 4.96 keV. In talc and kaolin, the element with the highest atomic number is silicon (Si), and therefore the absorption coefficient decreases steadily after the absorption limit of silicon at 1.8 keV with increasing energy of the radiation.

It is thus understood that when radiation having an energy higher than the K absorption limit of calcium is directed on a substance, for example, calcium, vacancies will form on the inner electron shells of the atoms. When these are filled by electrons falling from outer shells, the substance emits its characteristic K x-ray radiation, the energy of which because of recoil losses is slightly lower than the energy of the K-absorption limit. The strongest line of the calcium K has energy 3.69 keV, which has also been indicated on the energy axis in FIG. 1.

The characteristic x-ray radiation of each element produced through absorption is utilized in a manner known in the art in x-ray fluorescence analyses for determining the chemical composition of the specimens being analyzed. In the invention, the absorption is utilized towards determining the filler content of the paper's different layers and thus towards determining the filler distribution. In order that the determination of the distribution could be made sufficiently free of error from the viewpoint of the practical applications, the total contents of the different filler components in the paper must be known. This is determined, in the invention, by absorption measurements.

If, in the absorption measurements, the attenuation or extinction caused by paper containing filler is measured with two radiation energies which are as close as possible to the absorption limit of a given component in the manner that one energy is above and the other below the limit, the difference in the attenuation or extinction caused by the paper will furnish information about the content of such filler component. If the paper contains kaolin, talc, calcium carbonate and titanium oxide as fillers, the difference in the attenuation or extinction of the K line of manganese (5.9 keV) and of the K line of titanium (4.51 keV) will furnish information primarily about the titanium dioxide content (FIG. 2), the difference in the attenuation or extinction of the differences of the 4.51 keV (Ti K) and 3.69 keV (Ca K) radiations will furnish information primarily about the $CaCO_3$ content, and the absolute attenuation or extinction of the 3.69 keV radiation, primarily about the combined content of talc and kaolin, these latter components having absorption components which at the last-mentioned point are clearly higher than the absorption coefficients of any other components of the paper, as shown in FIG. 2.

In order to determine the contents of various filler components of paper, it is necessary to know the base weight of the whole paper, that is, its mass per unit area (in $g/m^2$). This is found by measuring the attenuation or extinction in the paper of beta radiation, for example, from an $^{85}Kr$ source. This is because the different components of paper cause equal attenuation or extinction of beta radiation, that is, of electrons thrown out by nuclei. The use of beta radiation for determining the base weight of paper is known in the art of paper technology and is completely routine in nature.

Figure 3:
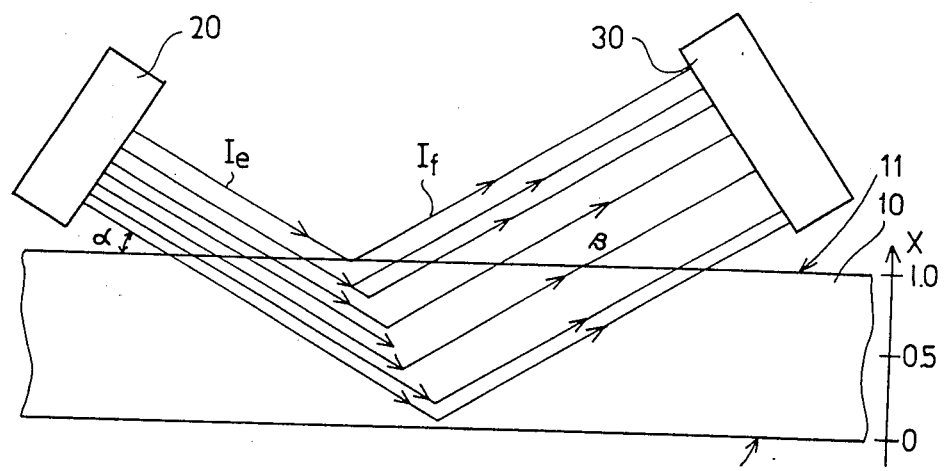
FIG. 3 is a schematic diagram illustrating the main principle of the fluorescence measurement of the invention.
Figure 4A:
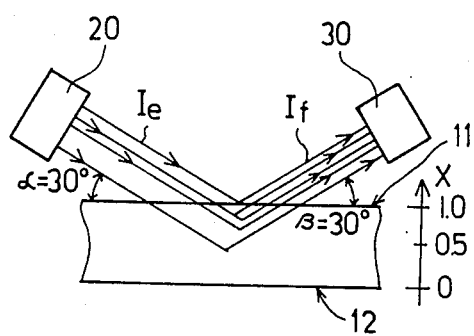
FIGS. 4A and 4B are schematic diagrams presenting the principle of the fluorescence measurement of the invention with two different angles of incidence of the exciting radiation and angles of departure of the excited radiation.
Figure 4B:
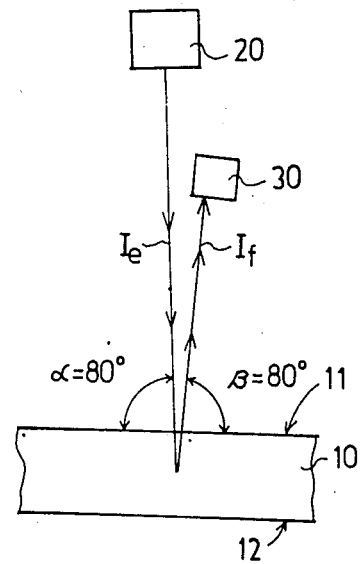

The fluorescence measurement used for the actual determination of the filler distribution is described more specifically with reference to FIG. 3, in connection with which it is assumed that the base weight of the paper specimen 10 is 100 $g/m^2$ and that it contains, as uniformly distributed filler, 25% calcium carbonate. As shown in FIG. 3, the exciting radiation $I_e$ from the source 20, which is an x-ray tube, impinges on the paper specimen at an angle of incidence $\alpha$ and excites in the specimen 10 the characteristic radiation of calcium, of 3.69 keV. The detector 30 measuring the radiation $I_f$ observes the radiation departing at an angle $\beta$ from the surface 11 of the specimen 10. Since the exciting radiation $I_3$ is attenuated as it proceeds in the paper specimen 10, it excites calcium radiation more efficiently in the adjacent top surface 11 which, which is to the source 20, than in the lower, or back, surface 12. Since the excited characteristic radiation of calcium is also attenuated in the specimen 10 to a given extent, the radiation excited adjacent the top surface 11 has easier access to the detector 30. Both of the just-mentioned circumstances act in the direction that the greater part of the radiation detected by the detector 20, in the case of homogeneous filler distribution, comes from the top layers of the specimen 10, and therefore the topmost layers of the paper will be emphasized in the information thus obtained. The smaller the angles of incidence and departure $\alpha$ and $\beta$ of the radiation, the greater are the differences in path length between the top surface 11 and the lower surface 12, and the greater is said stress placed on the top surface in the information gained by the detector 30. In this manner, it is possible, by varying the angles of incidence and departure $\alpha$ and $\beta$, to change the relative weight factors of different layers in the information that is measured. This is demonstrated by FIGS. 4A and 4B and by the following Table 1.

TABLE 1

| | | 80° | 30° |
|---|---|---|---|
| Angle of incidence of the radiation ($\alpha$) | | | |
| Angle of departure of the radiation ($\beta$) | | 80° | 30° |
| Relative intensity of information from different depths in the paper | Depth | Intensity | Intensity |
| | 0.05 | 0.93 | 0.86 |
| | 0.5 | 0.47 | 0.22 |
| | 0.95 | 0.23 | 0.06 |

Table 1 shows the relative intensity of the information received in fluorescence measurements at various depths in the specimen when two different pairs of angles of incidence and of departure, $\alpha,\beta$ of the radiation are used. The energy of the exciting radiation is equivalent on the average to the K line of manganese (5.9 keV). The base weight of the paper is 10 $g/m^2$ and its $CaCO_3$ content is 25%, assumed in this calculation example to be uniformly distributed in the vertical direction. On the depth scale, the surface is denoted by coordinate 0 and the back side of the paper is denoted by the value 1, making the coordinate of the center 0.5.

The intensity values calculated in Table 1 reveal that the information is strongly weighted in favor of the top side, in other words, emphasizing the side at which the measurement is performed. This effect is considerably strengthened upon changing the angles of incidence and departure of 80° in FIG. 4B one transfers to the angles $\alpha,\beta$ of 30° in FIG. 4A. This is seen when, for example, the values of the intensities obtained from the center of the paper (0.5) are mutually compared (0.47 and 0.22).

Another manner of varying the relative weighting of different layers of the specimen 10 is to change the energy of the radiation used for excitation, that is, of the radiation emitted by the x-ray tube 20. When this is done in the usual manner within a given measuring cycle, the fluorescence and absorption information required for determining the distribution is obtained simultaneously. This case will be examined in greater detail hereinafter.

If the distribution of a given filler component in the thickness direction of the specimen 10 is not uniform, but, for example like that shown in FIG. 1, the intensities of the characteristic radiation of calcium measured on different sides of the paper are unequal and their difference reflects the one-sidedness of the distribution. In the case of a paper having a distribution substantially like that of FIG. 1 and with a base weight of 160 g/m$^2$ and a calcium carbonate content of about 20%, with 5.0 keV radiation and using angles of incidence and of departure $\alpha, \beta = 80°$ on the average, the ratio of 470/410 of the intensities on different sides (top side/wire or lower side) was found. When the angles of incidence and departure were reduced, the ratio increased as could be expected. An effect in the same direction was achieved by using softer radiation of 4.5 keV.

The determination of the filler distribution on the basis of the results of measurement shall be considered.

The basic distribution as in FIG. 1, can be mathematically reprented by a polynomial $y = ax^2 + bx + c$, where y refers to filler content (ordinate) and x to the coordinate in the vertical direction of the paper (abscissa). The coefficients a, b and c are found by fitting to a reference distribution. The intensities of the characteristic radiation of calcium are determined from both sides of a paper with reference distribution to serve as reference values, and is the x-ray absorption of the paper at a suitable energy, and the beta absorption, such as, for example, a $^{85}$Kr source.

Then, when the equivalent quantities are measured from an unknown specimen belonging to the same paper brand, the differences between them and of the quantities measured from the reference paper will yield the filler distribution of the paper sample being measured, by mathematical methods, utilizing the known absorption coefficients of the different components. In the vicinity of the reference distribution, a measurement carried out with merely one pair of angles $\alpha, \beta$, or with one energy of the exciting radiation, provides a rather reliable estimate of the distribution. The reliability and accuracy can be increased by varying the angles of incidence and departure $\alpha, \beta$, or by using several different radiation energies. This naturally causes the mathematical processing to be more complicated.

In a case which was studied, the reference polynomial representing the filler distribution was found to be $y = -42x^2 + 52.1x + 6.7$, the unit y and of the coefficients a, b and c being the $CaCO_3$ content in %. It follows that the $CaCO_3$ according to the reference distribution, is 6.7% on the wire surface 12 (x=0) of the specimen 10, and 16.8% on the top surface 11 (x=1).

After the measurement results for the intensity I of the characteristic radiation of calcium, where $I_1$ is the wire side 12 and $I_2$ is the top side 11, and the result of the x-ray absorption measurement T for the paper specimen under examination have been corrected by applying the reference graph, with the aid of the results of the beta absorption measurements to correspond to the base weight of the reference paper, the changes $\Delta a, \Delta b, \Delta c$ of the coefficients of the distribution polynomial for the paper under examination can be calculated from the system of equations calculated from the reference polynomial.

$$\frac{\Delta I_1}{I_1} = 0.6113 \cdot \Delta a + 1.127 \cdot \Delta b + 3.344 \cdot \Delta c$$

$$\frac{\Delta I_2}{I_2} = 1.0403 \cdot \Delta a + 1.832 \cdot \Delta b + 2.781 \cdot \Delta c$$

$$\frac{\Delta}{T} = \frac{1}{2} \cdot \Delta a + \frac{1}{2} \cdot \Delta b + 1 \cdot \Delta c$$

In the system of equations, $\Delta I, \Delta Ia$ and $\Delta T$ correspond to the values of the paper specimen 10 under examination and to those measured from the reference paper.

In tests that have been carried out, the new coefficients obtained from the system of equations were found to yield distributions in agreement with the distributions determined from the same paper specimens by activation analysis close to the reference distribution. It is obvious that a more accurate approximation is attained by a greater number of measurements, but the accuracy afforded by the procedure described in the foregoing is adequate in certain supervision applications.

If in the example under consideration, kaolin, for example, is added to the filler of the paper in addition to calcium carbonate, as is frequently done intentionally or inadvertently in reused paper, etc., the situation is significantly altered in the sense of measuring technology. This is because kaolin attenuates, in fluorescence measurements, both the exciting $I_e$ and the excited $I_f$ radiation, especially the $I_f$ radiation, and as a result the variations of kaolin content affect to a certain degree the calcium carbonate measurements, even if the content and distribution of the calcium carbonate should be constant in the specimen 10. The influence of kaolin on the results is however calculable and can be eliminated with the aid of the known absorption coefficients, provided that the kaolin content in the specimen 10 is known. This leads to the requirement of measuring technology that, in connection with the measurements, the contents of kaolin and other potential filler components have to be determined. This is possible by using suitably selected radiation energies in the absorption measurements, as hereinbefore described. It may be observed, in this connection, that of the commonly used fillers, talc and kaolin are materials of which the contents must be determined by the absorption technique. Fluorescence measurements do not succeed in normal conditions because in these substances the characteristic x-ray radiation, even of the heaviest element, silicon (Si), is so weak that is is excessively attenuated in the specimen 10, in the air space and in the windows of standard detectors 30. The same methods for $CaCO_3$ may be applied for $TiO_2$, which is occasionally used, with the difference, of course, that the K line (4.51 keV) of titanium is excited and measured.

It is thus understood that in complicated cases the determination of the thickness-direction distribution of filler requires several x-ray fluorescence measurements on both sides of the specimen 10 and several absorption measurements. The intensity of the exciting radiation $I_e$ scattered back from the specimen 10, which correlates with several characteristics of the specimen paper may be used as a kind of control quantity in the measurements. In practice, when one is moving quite close to a given reference distribution, adequate accuracy is often achieved with rather few measurements.

If the x-ray tube 20 is so constructed that the energy of the radiation emitted therefrom can be varied during a measuring cycle T and the change of the measuring signal, or pulses per unit time may be recorded simultaneously as a function of the energy of the exciting radiation, the measuring activity may be considerably simplified.

Figure 5A:
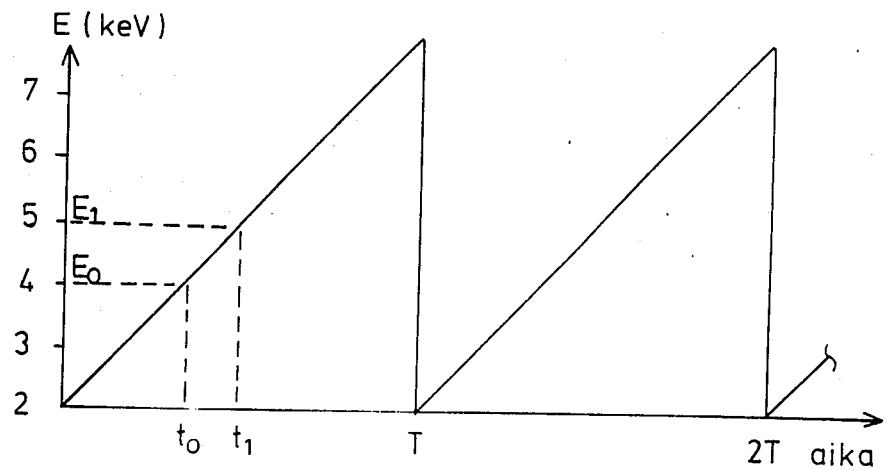
FIG. 5A is a graphical presentation of the variation of the average energy of the radiation emitted by an x-ray tube used in accordance with the first embodiment of the invention during the measuring cycle, as a function of time.
Figure 5B:
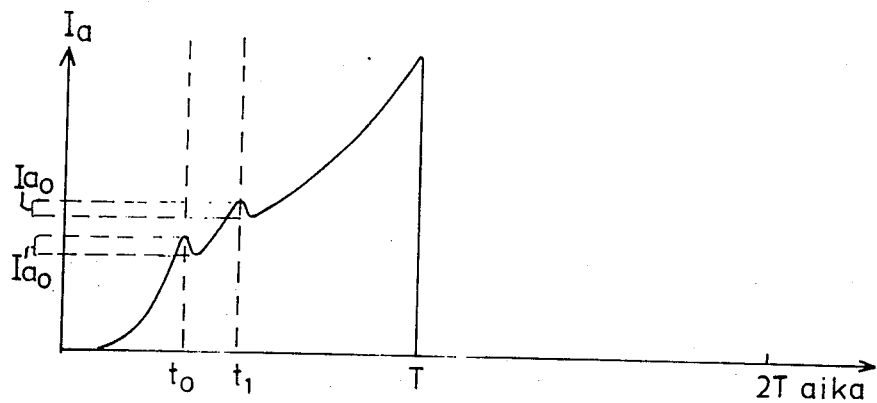
FIG. 5B is a graphical presentation of the count frequency recorded by the counter connected to the detector, in absorption measurements during one measurement cycle, as a function of time.

The energy of the radiation emitted by the x-ray tube 20 changes advantageously during one cycle of measurement, for example, as shown in FIG. 5A. If the paper specimen 10 contains kaolin, talc, calcium carbonate and titanium oxide as fillers, the pulse frequency observed by the counter 42 will vary in the radiation absorption measurements, as shown in FIG. 5B. When, at the beginning of the cycle T, the energy reaches a specific technical limit threshold, the counter 42 starts to observe pulses, and the count frequency increases uniformly at first, with increasing energy. When the energy reaches the K absorption limit of calcium $E_0 = 4.04$ keV, the count frequency falls after the respective time $t_o$, due to the discontinuously increasing absorption coefficient of calcium. Thereafter, with a further increase in the energy of the radiation, the count frequency decreases smoothly until the K absorption limit $E_1 = 4.9$ keV of titanium is reached, after the respective time $t_1$ a decrease in the count frequency ensuing, caused by the discontinuous increase of the absorption coefficient of titanium. By using the magnitude of the step $E_1 - E_0$ (FIG. 5A) and the differences of count frequency $Ia_o$ and $Ia_1$ (FIG. 5B), and the absorption measurement carried out by the beta radiation, for example, $^{85}Kr$, the base weight of the paper specimen 10 is found. The contents of calcium carbonate and titanium dioxide and the combined contents of talc and kaolin, are also found for the corrections by calculation of the fluorescence measurements required in the determinations of distribution. In practice, it is difficult, or even impossible, to alter the energy of the radiation emitted by the x-ray tube 20 in the ideal and monochromatic manner shown in FIG. 5A. If, however, the pulse frequencies Ia recorded by the counter 42 on the average correspond to energies between which the absorption jumps fall, the results will, with appropriate calibration measurements, usually furnish the filler contents with sufficient accuracy.

Figure 5C:
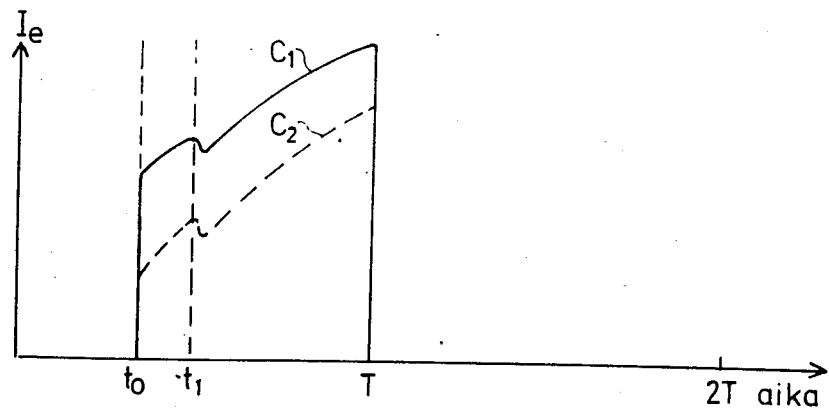
FIG. 5C is a graphical presentation of the count frequency of the fluorescence signals (Ca K line) during one measuring cycle as a function of time.

In the fluorescence measurements constituting the basis for the determinations of distribution, the count frequency $I_3$ of the counter 42 changes during the measuring cycle, as shown in FIG. 5C. The filler distribution is assumed to be the same as in FIG. 1, and the object of examination is the observed intensity of the calcium K line excited in the paper specimen. The solid-line curve $C_1$ of FIG. 5C corresponds to the measurement from the top side of the paper specimen (x=1), and the interrupted line curve $C_2$ similarly represents the measurement from the underside of the paper. When, at the beginning of the measuring cycle T, the energy of the exciting radiation is lower than the K absorption limit of calcium, no characteristic radiation of calcium at all will, of course, be produced in the paper. When this limit is just surpassed at the time $t_o$, the signal measured at the top side of the specimen (x=1) will, in accordance with FIG. 5C, rise to be clearly higher than the signal measured on the wire side (x=0), because soft radiation "sees" more calcium on the top side. As the energy of the radiation increases, the signals measured at the top side and at the wire side, as shown in curves $C_1$ and $C_2$, approach each other, however. Thus, even with high exciting radiation energies the signal measured at the top side remains higher than that obtained at the wire side, due to the absorption of excited radiation occurring in the paper. At the point $t_1$ corresponding to the K absorption limit of titanium $E_1 = 4.96$ keV, there is a small dip in the curves $C_1$ and $C_2$ due to the increasing matric absorption.

The pulse frequencies $I_e$ selected at a suitable point in FIG. 5C correspond to the count frequencies $I_1$ and $I_2$ excited with constant energy at different sides of the paper in the preceding examples, and they can therefore be used in the mathematical procedures presented for determining the distributions. This measuring technique has the advantage that during the measuring cycle a great number of such intensity pairs $I_1$, $I_2$ are obtained as a function of the exciting radiation. With the aid of these intensity pairs, more detailed information about the course of the distribution is obtained by more advanced mathematical considerations. Furthermore, it is naturally necessary to carry out corrections for eliminating the effects from the filler components' variations in relation to each other on the basis of the total contents determined by absorption measurements. As hereinbefore mentioned in connection with the absorption measurements, it is difficult, or even impossible in practice, to change the energy of the radiation emitted by the x-ray tube 20 in such ideal and monochromatic manner during one measuring cycle, as has been shown in FIG. 5A. However, in practice, even with a less ideal cycle T, in which intensity pairs are obtained corresponding to a few average energies, adequate information is obtained for determining the distribution.

As the preceding consideration reveals, an exciting energy E varying within the measuring cycle T supplies considerably more information about the distribution and about the contents of the filler components than an exciting source with constant energy. However, the variable energy imposes rather more exacting demands on the electronics of the measuring apparatus, in that it is necessary in this instance to record a continuously varying count frequency during the cycle T, and simply counting the accumulated number of pulses is inadequate.

Figure 6A:
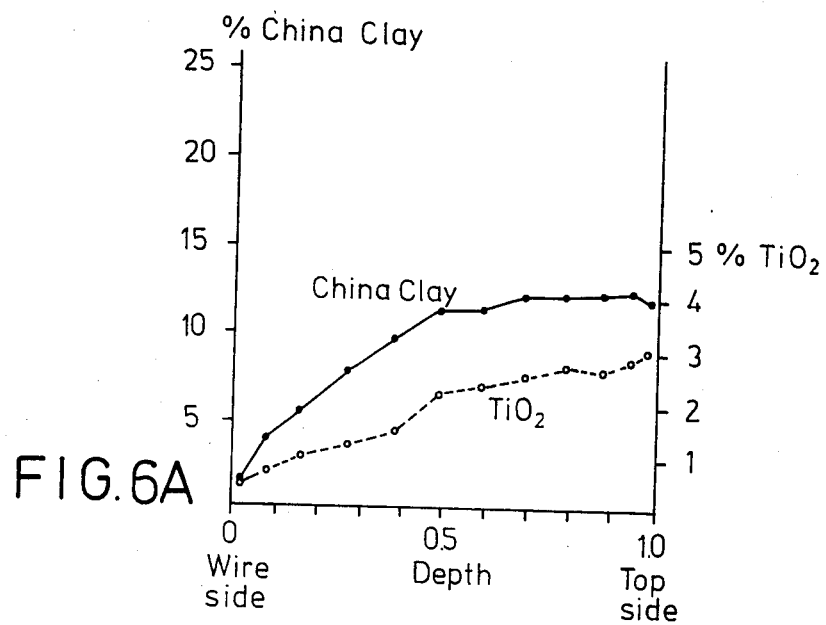
FIG. 6A is a graphical presentation of the distribution of filler components prior to coating the paper.
Figure 6B:
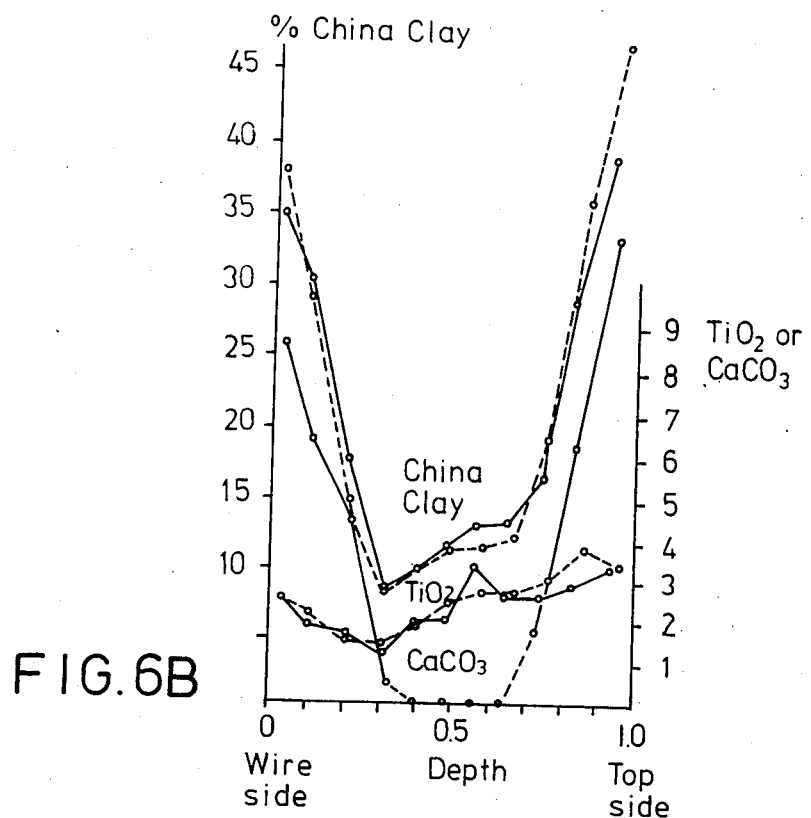
FIG. 6B is a graphical presentation of the same paper after the coating process.

The printing characteristics of paper can be improved by coating the paper with the same substances that are used as fillers. In this case, the contents of mineral components in the surface layers of the paper increases greatly, as seen in FIGS. 6A and 6B hereinbefore discussed. Since the method of the invention provides information about the distribution of the mineral components in the paper and, in particular, about their content in the surface layers of the papers, it is also possible to determine the amount of coating in the coating layers and the difference in coating between the different sides of the paper by the method of the invention without destroying the specimen. If the paper is already coated, the filler distribution of the uncoated bottom paper naturally cannot be elicited any longer.

Figure 7:
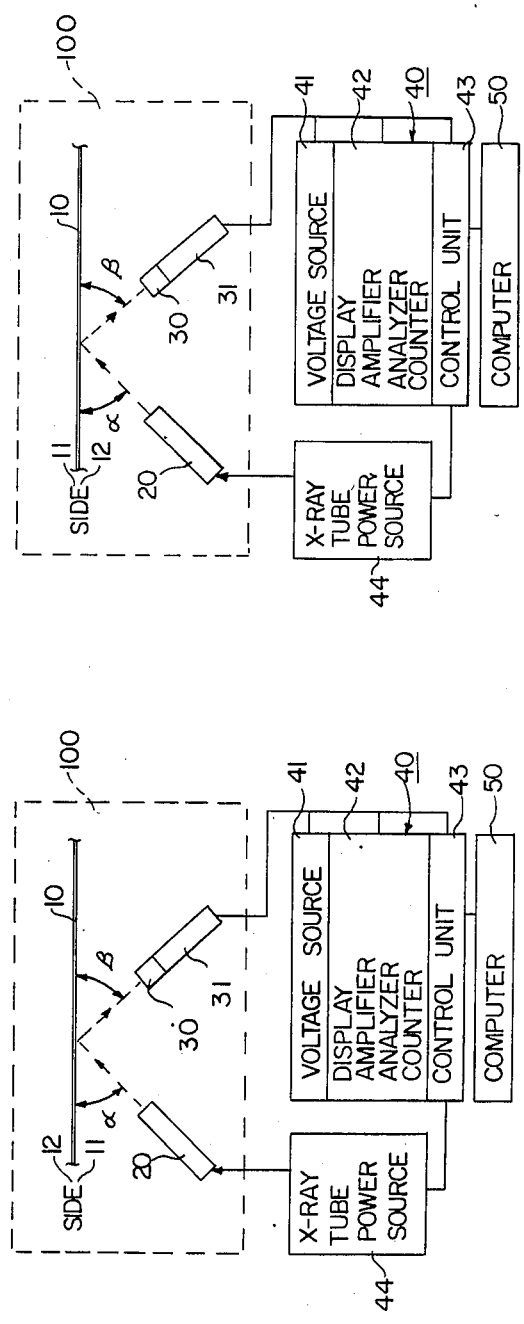
FIG. 7A is a schematic diagram of an embodiment of the apparatus of the invention and its measuring head, wherein an x-ray tube emitting constant energy radiation is applied.
FIG. 7B is a schematic diagram of a second embodiment of the apparatus of the invention in an arrangement by which absorption measurements are carried out with x-ray radiation of different energies.
FIG. 7C is a schematic diagram of a third embodiment of the measuring apparatus of the invention and its measuring head, wherein an x-ray tube emitting radiation of varying energy during the measuring cycle is applied.
FIG. 7D is a schematic diagram of a fourth embodiment of the apparatus of the invention, utilizing the beta absorption measurement by which the auxiliary quantity required in the invention is produced.
Figure 7C:
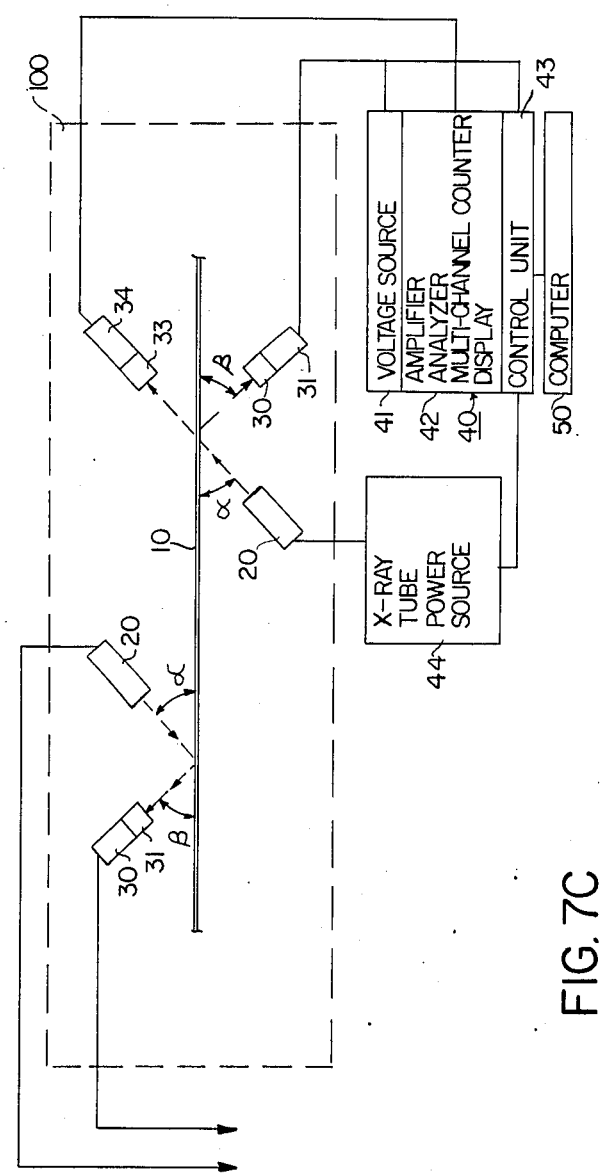

The measurement and apparatus of the invention is presented in FIGS. 7A, 7B 7C and 8. FIG. 7A illustrates the x-ray fluorescence measurement by an x-ray tube 20 emitting radiation of constant energy. FIG. 7B shows the equivalent absorption measurement. It is naturally required that a fluorescence measurement be performed on both sides of the paper. FIG. 7C shows apparatus for measurement carried out with an x-ray tube 20 emitting radiation varying in energy within the measuring cycle T, as shown in FIG. 5A. The fluorescence measurement on one side of the paper and the absorption measurement may then be accomplished simultaneously. In this instance as well, a separate fluorescence measurement has naturally to be carried out at the other side of the paper.

The part isolated by interrupted lines in FIGS. 7A, 7B and 7C is the measuring head 100. The measuring head 100 comprises the x-ray tube 20 having a device, if any, for changing the angle of incidence of the exciting radiation $I_e$, a detector 30 with pre-amplifier 31, and, in the case of the x-ray tube 20 emitting constant energy radiation, also a transfer mechanism 22 for the radiation transformation target 21. In laboratory apparatus, the measuring head 100 is, for example, an enclosed apparatus on the table, into which the paper specimen 10 to be examined is conveyed by a suitable mechanism. In an on-line apparatus accomplishing the measurements directly in the paper machine, as shown in FIG. 8 the paper web 200 passes through the measuring head 100 mounted on a measuring beam 300. The measuring head 100 may be so constructed that it may traverse the paper web, as shown in FIG. 8.

The detector 30 principally consists of a proportional counter or a scintillation crystal. In certain instances, in particular, in laboratory measurements, a semiconductor counter may also be used with a view to increasing the accuracy.

When an x-ray tube emitting constant energy radiation is used (FIGS. 7A and 7B), the measuring head 100 is connected to measuring apparatus 40 comprising a voltage source 41, an amplifier and a counter, processor and display unit 42, and to the power and control unit 44 of the x-ray tube. A control unit 43 connected to a processor or computer 50 controls the performing of measurements and the processing of results. In the laboratory version, the processor operations may, of course, be replaced by manual operations and the results may, of course, be processed manually, or by an external computer. When using an x-ray tube 20 emitting radiation varying in its energy during the measuring cycle T, it is necessary to use a multi-channel counter applying a time axis instead of the counter 42.

The extent of the equipment external to the measuring head 100 and of the software and programs for the computer 50 is greatly dependent upon the degree of automation and the standard of accuracy desired at, and on the extent of the measuring range, that is, the number of different paper brands and the variation limits, within each brand, of the quantities which are measured.

FIG. 7A illustrates the exciting of the characteristic fluorescence radiation of a filler component ($CaCO_3$ or $TiO_2$) and its measuring at the other side of the paper specimen 10. The radiation $I_e$ emitted by the radiation source 20 excites in the paper specimen 10 the characteristic x-ray radiation of a given element (Ca or Ti) of a filler, part of which is directed to the detector 30 and counted. The detector 30 differentiates between the different types of radiation by their energy with such accuracy that the contribution of each radiation component can be determined from the measured pulse height distribution by mathematical means. If it is desired to make the measurement at different angles of incidence and departure of the radiation with reference to the surface of the paper specimen 10, movable collineators or radiation beam detectors may be used.

Since, for determining the distribution, a fluorescence measurement has to be made at both sides 11 and 12 of the paper, in the laboratory version, the paper specimen 10 must be turned over, or two measuring heads 100 carrying out measurement at different sides of the paper have to be used. When measurements are carried out directly in the paper machine, is the only possible alternative is the two heads.

FIG. 7B presents an arrangement by which absorption measurements are carried out with x-ray radiation of different energies. The radiation from the x-ray tube 20 that has passed through the paper specimen 10 excites a radiation in the backing plate 21 suitable for absorption measurements and which passes partly through the paper specimen 10 to the detector 30. In this instance, the signal of the radiation excited in the paper specimen 10 by the source is admixed with the signal being measured. The signal of the radiation excited in the specimen 10 reduces the accuracy of measurement in certain cases.

FIG. 7C represents the measurement performed with an x-ray tube 20 emitting radiation of varying energy during the measuring cycle. In the measurement apparatus of FIG. 7C, the measuring of fluorescence is at the same side of the specimen 10 where the x-ray tube 20 is located and the absorption measurement is at the opposite side of said specimen, using an absorption detector 33 and a pre-amplifier 34 connected to said detector accomplished simultaneously.

Figure 7D:
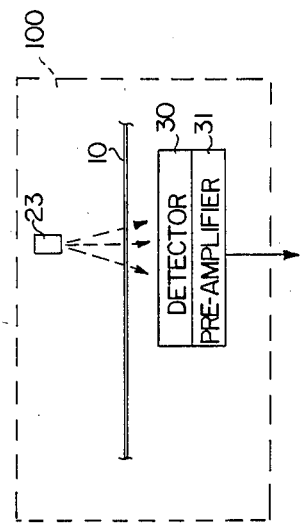

FIG. 7D presents beta absorption measurement apparatus used as routine in the papermaking industry for base weight measurements and which in the distribution measurements supplies the auxiliary quantity indispensable in the processing of the results. These auxiliary measurements are accomplished using a beta source 23, a detector 30 and a pre-amplifier 31 in the manner known in the art.

FIG. 8 is a schematic diagram of a measuring head 100 mounted on a transverse measuring beam 300 in a paper machine to perform on-line measurement traversing reciprocatingly the width of the travelling paper web 200.

Detailed reference distributions which are indispensable for demonstrating and proving the practical applicability of the method of the invention may be determined by neutron activation analysis of microtome sections made of paper. The technique is described in an article by Kuusi J. and Lehtinen, A. J. entitled, "Neutron Activation Analysis of Microtome Cuts in Examination of Paper for Its Filler Distribution", Pulp and Paper Magazine of Canada, 71, No. 3 (1970).

The method and apparatus hereinbefore described are suitable for use either in laboratory measurements or on-line measurements in a paper machine. In the on-line measurement use, the results obtained by the measuring apparatus may be used as feedback signals for guiding and/or controlling the papermaking process towards implementing desired filler distribution. A possible application of the invention is the use of the method or apparatus in the measurement, and possibly even in the control, of the coating agent content and/or coating distribution either of paper or cardboard to be coated in an on-line process, or of paper treated in separate coating means, in particular of its onesidedness. Further applications of the invention may be the quality control of paper fed into a printing press, and even the guiding, or control, of the operation of a printing press for optimizing the printing quality and minimizing trouble encountered in the operation of the printing press.

The invention is by no means restricted to the aforementioned details which are described only as examples; they may vary within the framework of the invention, as defined in the following claims.

It will thus be seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A method of measuring, without destroying the specimen, the distribution in the thickness direction of the filler and/or coating materials of paper or cardboard, and the content of said materials, wherein radiation emitted by an X-ray tube is used to excite in the material component to be examined, of the object of measurement, its characteristic X-ray radiation, the intensity of said characteristic radiation being observed, measurements are made on both sides of the paper or cardboard under examination, the contents of said materials are determined by X-ray absorption measurements for eliminating the effects of these components disturbing the distribution measurement, and measurement is made of the base weight of the paper or cardboard under examination by radiation absorption, said method comprising the steps of
making a number of X-ray absorption measurements, the number of measurements being at least equal to the number of different filler components, for determining the contents of the different filler components and the coating materials by means of constant energy X-ray radiation;
making a number of measurements of the characteristic X-ray fluorescent radiation of the material components excited via the X-ray tube of the paper or cardboard; and
determining the distributions of fillers and coating materials by calculative joint processing of the results from said measurements.

2. A method as claimed in claim 1, wherein radiation is obtained directly from said X-ray tube.

3. A method as claimed in claim 1, wherein radiation is provided by use of a transformation target.

4. A method as claimed in claim 1, said method further comprising the step of determining the intensity of the radiation from said X-ray tube scattered back from the paper or cardboard, which correlates with the base weight of the paper or cardboard, so as to provide an auxiliary quantity in the processing of results, in addition to X-ray fluorescence measurements.

5. A method as claimed in claim 1, wherein the contents of various filler components are measured by X-ray absorption measurements utilizing the primary radiation emitted by said X-ray tube and radiation with specific absorption properties derived from said primary radiation via a transformation target.

6. A method as claimed in claim 5, wherein the filler material of said paper or cardboard under examination is principally kaolin, talc, calcium carbonate and/or titanium dioxide, said method utilizing the characteristic 5.9 keV K line excited by the primary radiation source in the manganese of said transformation target, the characteristic 4.51 keV K line excited in the titanium of said transformation target and the calcium 3.69 keV K line excited in the calcium of said transformation target, and using the difference encountered between the extinction of said characteristic 5.9 keV K line in said manganese and of said characteristic 4.51 keV K line excited in said titanium primarily in determining the titanium dioxide content, utilizing the absorption difference observed in the extinctions of said K line of said titanium and said 3.69 keV K line of said calcium primarily in determining the $CaCO_3$ content, and using the information provided by the attenuation of said calcium K line primarily for determining the combined content of talc and kaolin.

7. A method as claimed in claim 1, further comprising the step of measuring the attenuation in the object under measurement of beta rays emitted by an $^{85}Kr$ source to determine the base weight in $g/m^2$ of said paper.

8. A method as claimed in claim 1, wherein said measurements are carried out with at least two angles of incidence ($\alpha$) of the exciting radiation emitted by said X-ray tube.

9. A method as claimed in claim 8, wherein said measurements are carried out with at least two angles of departure ($\beta$) of the characteristic X-ray radiation excited in the specimen by the radiation emitted by said X-ray tube.

10. A method as claimed in claim 9, wherein the angle of incidence ($\alpha$) of said radiation is equal in magnitude to the angle of departure ($\beta$) of the excited radiation relative to the plane of said paper or cardboard on the same side of said paper or cardboard.

11. A method of measuring, without destroying the specimen, the distribution in the thickness direction of the filler and/or coating materials of paper or cardboard, and the content of said materials, wherein radiation emitted by an X-ray tube is used to excite in the material component to be examined, of the object of measurement, its characteristic X-ray radiation, the intensity of said characteristic radiation being observed, measurements are made on both sides of the paper or cardboard under examination, the contents of filler components are determined by X-ray absorption measurements for eliminating the effects of these components disturbing the distribution measurement, and measurement is made of the base weight of the paper or cardboard under examination by radiation absorption, said method comprising the steps of
making a number of X-ray absorption measurements, the number of measurements being at least equal to the number of different filler components, for determining the contents of the different filler components and the coating materials by means of radiation varying in energy during a measuring cycle;
making a number of measurements of the characteristic X-ray fluorescent radiation of the material components excited via the X-ray tube in the paper or cardboard; and
determining the distributions of fillers and coating materials by calculative joint processing of the results from said measurements.

12. A method as claimed in claim 11, wherein radiation is obtained directly from said X-ray tube.

13. A method as claimed in claim 11, wherein radiation is provided by use of a transformation target.

14. A method as claimed in claim 11, further comprising the step of recording the variation of intensity of an observed signal during a measuring cycle of fluorescent measurement and absorption measurements, as a function of the variation of the energy of the radiation emitted by said X-ray tube.

15. A method as claimed in claim 11, wherein the filler material of said paper or cardboard under examination is principally kaolin, talc, calcium carbonate and/or titanium dioxide, the K absorption limit of titanium is 4.96 keV and the K absorption limit of calcium is 4.04 keV, said method utilizing the difference in the intensities of the signals corresponding to energies of the exciting radiation above and below said K absorption limit of titanium to determine the titanium dioxide content in absorption measurements, utilizing the difference of the signals of the exciting radiation measured on both sides of said K absorption limit of calcium to determine the content of calcium carbonate, and utilizing the equivalent attenuation of the signal measured at an energy lower than the K absorption limit of calcium primarily to determine the combined content of kaolin and talc.

16. A method as claimed in claim 11, further comprising the step of measuring the contents of different filler components by measuring X-ray absorption utilizing the variation during the measuring cycle of the intensity of the signal derived in the absorption measurements as a function of the variation in energy of the radiation emitted by said X-ray tube when said energy varies, so that the range of variation of the average energy covers at least the energy range from 3 to 8 keV.

17. Apparatus for measuring the distribution in the thickness direction and the content of said materials of filler and/or coating materials of paper or cardboard, without destroying the specimen, said apparatus including means having an X-ray tube emitting radiation which excites in the material component under examination, of the object of measurement, its characteristic X-ray fluorescent radiation, means for observing the intensity of said characteristic radiation, means for performing measurements on both sides of the paper or cardboard under examination and for determining the contents of filler components by X-ray absorption measurements for eliminating the effects of these components disturbing the distribution measurement, and means for measuring the base weight of the paper or cardboard under examination by beta radiation absorption measurement, said apparatus comprising a measuring unit having power sources, amplifiers, a counter, a processor and a display unit; and a measuring head connected to said measuring unit, said measuring head having an X-ray tube emitting constant energy radiation, radiation transforming plates, transfer means for said plates, radiation detectors and pre-amplifiers connected to each other in a manner whereby they perform X-ray absorption measurements for the determination of the contents of the different filler components by utilizing radiation directly from said X-ray tube or radiation excited with its aid in suitable transformation targets and measurements of characteristic radiation of different material components in paper or cardboard excited by said X-ray tube.

18. Apparatus as claimed in claim 17, wherein said measuring head in disposed to traverse reciprocatingly over the entire width of the specimen or part thereof.

19. Apparatus as claimed in claim 17, wherein said measuring unit further comprises a control unit which controls the carrying out of the measurements and the processing of results.

20. Apparatus as claimed in claim 17, wherein said radiation detectors in said measuring head comprise proportional counters.

21. Apparatus as claimed in claim 17, wherein said radiation detectors in said measuring head comprise semiconductor counters.

22. Apparatus as claimed in claim 17, further comprising a computer connected to said measuring unit, said computer being programmed with a measurement result-processing and outputting program.

23. Apparatus as claimed in claim 17, further comprising a control unit connected to said measuring head, said control unit controlling the carrying out of the measurement cycle.

24. Apparatus for measuring the distribution in the thickness direction and the content materials of filler and/or coating materials of paper or cardboard, without destroying the specimen, said apparatus including means having an X-ray tube emitting radiation which excites in the material component under examination, of the object of measurement, its characteristic X-ray radiation, means for observing the intensity of said characteristic radiation, means for performing measurements on both sides of the paper or cardboard under examination and for determining the contents of filler components by X-ray absorption measurements for eliminating the effects of these components disturbing the distribution measurement, and means for measuring the base weight of the paper or cardboard under examination by radiation absorption measurement, said apparatus comprising a measuring unit having power sources, amplifiers, a multichannel counter, a processor and a display unit using a time axis; and a measuring head connected to said measuring unit, said measuring head having an X-ray tube emitting radiation varying in energy during a measuring cycle, radiation detectors and preamplifiers connected to each other in such manner as to determine the contents of the different filler components via radiation directly from said X-ray tube and varying in energy during the measuring cycle and measure absorption and the characteristic radiation of the material component excited in the paper or cardboard by said radiation from said tube.

25. Apparatus as claimed in claim 24, further comprising a control unit connected to said measuring head for controlling the carrying out of the measurement cycle.

26. Apparatus as claimed in claim 24, wherein said measuring unit further comprises a control unit which controls the carrying out of the measurements and the processing of results.

27. Apparatus as claimed in claim 24, wherein said radiation detectors in said measuring head comprise proportional counters.

28. Apparatus as claimed in claim 24, wherein said radiation detectors in said measuring head comprise semiconductor counters.

29. Apparatus as claimed in claim 24, further comprising a computer connected to said measuring unit, said computer being programmed with a measurement result-processing and outputting program.

* * * * *